(12) United States Patent
Cotter et al.

(10) Patent No.: US 9,421,027 B2
(45) Date of Patent: *Aug. 23, 2016

(54) METHOD OF CREATING A SHEAR STRESS FIELD WITH MEDICAL DEVICE

(71) Applicant: Integra LifeSciences (Ireland) Ltd., Tullamore (IE)

(72) Inventors: Daniel J. Cotter, North Easton, MA (US); Saurav V. Gupta, Needham, MA (US); James P. O'Connor, Billerica, MA (US); Matthew F. Shinopulos, Burlington, MA (US)

(73) Assignee: Integra Lifesciences (Ireland) Ltd., Tullamore (IE)

(*) Notice: Subject to any disclaimer, the term of this patent is extended or adjusted under 35 U.S.C. 154(b) by 68 days.

This patent is subject to a terminal disclaimer.

(21) Appl. No.: 14/010,512

(22) Filed: Aug. 26, 2013

(65) Prior Publication Data

US 2013/0345734 A1 Dec. 26, 2013

Related U.S. Application Data

(60) Continuation of application No. 13/325,999, filed on Dec. 14, 2011, now Pat. No. 8,518,066, which is a division of application No. 12/395,417, filed on Feb. 27, 2009, now Pat. No. 8,118,823.

(60) Provisional application No. 61/061,055, filed on Jun. 12, 2008.

(51) Int. Cl.
*A61B 17/32* (2006.01)
*A61B 17/3205* (2006.01)

(52) U.S. Cl.
CPC ... *A61B 17/320068* (2013.01); *A61B 17/32053* (2013.01); *A61B 2017/320072* (2013.01); *A61B 2217/005* (2013.01)

(58) Field of Classification Search
CPC .............. A61B 17/2212; A61B 17/32; A61B 17/320068; A61B 17/320092; A61B 17/320096; A61B 17/32053; A61B 2017/320072; A61B 2017/32008–2017/320088; A61B 2017/320076; A61B 2217/005; A61C 3/03; A61F 9/00736; A61F 9/00754; A61F 9/00763; A61F 9/00745
USPC ............ 604/22; 606/107, 127, 128, 159, 161, 606/162, 169; 623/6.12
See application file for complete search history.

(56) References Cited

U.S. PATENT DOCUMENTS

| | | |
|---|---|---|
| 4,063,557 A | 12/1977 | Wuchinich et al. |
| 5,188,102 A | 2/1993 | Idemoto et al. |
| 5,199,943 A | 4/1993 | Wypych |
| 5,221,282 A | 6/1993 | Wuchinich |

(Continued)

*Primary Examiner* — David C Eastwood
(74) *Attorney, Agent, or Firm* — Thomas A. Runk; Fulwider Patton LLP (57) ABSTRACT

An ultrasonic horn for use with an ultrasonic surgical hand piece including a resonator comprises a contacting annulus having a plurality of angled lands. The lands are alternated around the annulus such that adjacent lands have opposite angles. As a result of the adjacent angled lands, a shear stress field is developed in contacted tissue due to the promotion of refracted longitudinal ultrasonic waves propagating in different directions at the interface to the coupled tissue. The shear stress field enhances the fragmentation and removal rate of fibrous, elastic, and tenacious tissue. The horn is hollow permitting suction to be applied to the tissue for controlling tissue contact with the lands.

16 Claims, 8 Drawing Sheets

(56) References Cited

U.S. PATENT DOCUMENTS

| | | |
|---|---|---|
| 5,318,570 A | 6/1994 | Hood et al. |
| 5,417,654 A | 5/1995 | Kelman |
| 5,464,389 A | 11/1995 | Stahl |
| 5,562,609 A | 10/1996 | Brumbach |
| 5,562,610 A | 10/1996 | Brumbach |
| 5,674,235 A | 10/1997 | Parisi |
| 5,746,756 A | 5/1998 | Bromfield et al. |
| 5,836,959 A | 11/1998 | Seibel et al. |
| 5,879,364 A | 3/1999 | Bromfield et al. |
| 5,980,529 A | 11/1999 | Strukel |
| 6,074,396 A * | 6/2000 | Geuder .................. 606/107 |
| 6,165,150 A | 12/2000 | Banko |
| 6,214,017 B1 | 4/2001 | Stoddard et al. |
| 6,241,703 B1 | 6/2001 | Levin et al. |
| 6,254,622 B1 | 7/2001 | Hood |
| 6,368,299 B1 | 4/2002 | Cimino |
| 6,497,715 B2 | 12/2002 | Satou |
| 6,533,750 B2 | 3/2003 | Sutton et al. |
| D478,383 S | 8/2003 | Timm et al. |
| 6,695,847 B2 | 2/2004 | Bianchetti et al. |
| 6,723,110 B2 | 4/2004 | Timm et al. |
| D497,992 S | 11/2004 | Timm et al. |
| D511,002 S | 10/2005 | Easley |
| 7,004,282 B2 | 2/2006 | Manna et al. |
| D551,764 S | 9/2007 | Easley |
| D558,876 S | 1/2008 | Spetzler et al. |
| 7,374,552 B2 | 5/2008 | Wuchinich |
| 8,118,823 B2 * | 2/2012 | Cotter et al. .................. 606/169 |
| 8,518,066 B2 * | 8/2013 | Cotter et al. .................. 606/169 |
| 2001/0011176 A1 | 8/2001 | Boukhny |
| 2002/0156492 A1 * | 10/2002 | Timm et al. .................. 606/169 |
| 2003/0212331 A1 | 11/2003 | Fenton et al. |
| 2005/0187514 A1 | 8/2005 | Rabiner et al. |
| 2006/0004396 A1 | 1/2006 | Easley et al. |
| 2006/0041220 A1 | 2/2006 | Boukhny et al. |
| 2006/0052758 A1 | 3/2006 | Dewey |
| 2006/0235305 A1 | 10/2006 | Cotter et al. |
| 2006/0235306 A1 | 10/2006 | Cotter et al. |
| 2006/0241470 A1 | 10/2006 | Novak et al. |
| 2006/0253056 A1 | 11/2006 | Kadziauskas et al. |
| 2006/0264970 A1 | 11/2006 | Ernest et al. |
| 2008/0058585 A1 | 3/2008 | Novak et al. |
| 2008/0058775 A1 | 3/2008 | Darian et al. |
| 2008/0132927 A1 * | 6/2008 | Sakai .................. 606/169 |
| 2008/0300591 A1 | 12/2008 | Darian et al. |

* cited by examiner

METHOD OF CREATING A SHEAR STRESS FIELD WITH MEDICAL DEVICE

CROSS-REFERENCES TO RELATED APPLICATIONS

This application is a continuation of U.S. application Ser. No. 13/325,999, filed Dec. 14, 2011, which is a divisional application of U.S. application Ser. No. 12/395,417, filed Feb. 27, 2009, now U.S. Pat. No. 8,118,823, that claims the benefit of U.S. Provisional Application No. 61/061,055, filed Jun. 12, 2008, all of which are incorporated herein by reference in their entireties.

BACKGROUND OF THE INVENTION

The present invention relates generally to ultrasonic surgical devices, and more particularly, to ultrasonic surgical devices useful for removing fibrous, elastic, or tenacious tissue.

Devices that effectively utilize ultrasonic energy for a variety of applications are well known in a number of diverse arts. One of these devices is an ultrasonic horn used for the removal of tissue. The Ampulla or Gaussian profile was published by Kleesattel as early as 1962, and is employed as a basis for many ultrasonic horns in surgical applications including devices described in U.S. Pat. No. 4,063,557 to Wuchinich, et al, 1977, and U.S. Pat. No. 6,214,017 to Stoddard, et al, 2001 for use in ultrasonic aspiration. The Gaussian profile is used in practice to establish and control the resonance and mechanical gain of horns. A resonator, a connecting body, and the horn act together as a three-body system to provide a mechanical gain, which is defined as the ratio of output stroke amplitude of the distal end of the tip to the input amplitude of the resonator. The mechanical gain is the result of the strain induced in the materials of which the resonator, the connecting body, and the ultrasonic horn are composed.

A magnetostrictive transducer coupled with the connecting body functions as a first stage of the booster horn with a mechanical gain of about 2:1, due to the reduction in area ratio of the wall of the complex geometry. The major diameter of the horn transitions to the large diameter of the Gaussian segment in a stepped-horn geometry with a gain of as large as about 5:1, again due to reduction in area ratio. The uniform strain along the length of the Gaussian provides multiplicative gain of typically less than 2:1. Thus, the application of ultrasonically vibrating surgical devices used to fragment and remove unwanted tissue with significant precision and safety has led to the development of a number of valuable surgical procedures. Accordingly, the use of ultrasonic aspirators for the fragmentation and surgical removal of tissue from a body has become known. Initially, the technique of surgical aspiration was applied for the fragmentation and removal of cataract tissue. Later, such techniques were applied with significant success to neurosurgery and other surgical specialties where the application of ultrasonic technology through a handheld device for selectively removing tissue on a layer-by-layer basis with precise control has proven feasible.

Certain devices known in the art characteristically produce continuous vibrations having substantially constant amplitude at a predetermined frequency (i.e. 20-36 kHz). Certain limitations have emerged in attempts to use such devices in a broad spectrum of surgical procedures. For example, the action of a continuously vibrating tip may not have an adequate effect in breaking up certain types of body tissue, more elastic tissue, bone, etc. Because the ultrasonic frequency is limited by the physical characteristics of the handheld device, only the motion available at the tip provides the needed motion to break up a particular tissue. All interaction with the tissue is at the tip, some is purely mechanical, and some is ultrasonic. Some teach in the art that interaction with the tissue at the tip distal and is due only to mechanical interaction. To others, it is clear from experimental results that acoustic power is propagated to the load to aid in tissue fragmentation, emulsification, and aspiration. In any case, the devices have limitations in fragmenting some tissues. The limited focus of such a device may render it ineffective for certain applications due to the vibrations which may be provided by the handheld device. For certain medical procedures, it may be necessary to use multiple hand held devices or it may be necessary to use the same console for powering different handheld devices.

Certain devices known in the art characteristically produce continuous vibrations having substantially constant amplitude at a frequency of about twenty to about fifty-five kHz. Amplitude of transducer-surgical tip systems decreases with increasing frequency because maximum stress in the material of the horns is proportional to amplitude times frequency, and the material must be maintained to an allowed fraction of its yield strength to support rated life in view of material fatigue limits. For example, U.S. Pat. Nos. 4,063,557, 4,223,676 and 4,425,115 disclose devices suitable for the removal of soft tissue which are particularly adapted for removing highly compliant elastic tissue mixed with blood. Such devices are adapted to be continuously operated when the surgeon wishes to fragment and remove tissue, and generally is operated by a foot switch.

A known instrument for the ultrasonic fragmentation of tissue at an operation site and aspiration of the tissue particles and fluid away from the site is the CUSA EXcel® Ultrasonic Surgical Aspirator (Integra LifeSciences Corporation, Plainsboro, N.J.). When the longitudinally vibrating tip in such an aspirator is brought into contact with tissue, it gently, selectively, and precisely fragments and removes the tissue. The CUSA® transducer amplitude can be adjusted independently of the frequency and this amplitude can be maintained under load depending on reserve power of the transducer. In simple harmonic motion devices, the frequency is independent of amplitude. Advantages of this unique surgical instrument include minimal damage to healthy tissue in a tumor removal procedure, skeletoning of blood vessels, prompt healing of tissue, minimal heating or tearing of margins of surrounding tissue, minimal pulling of healthy tissue, and excellent tactile feedback for selectively controlled tissue fragmentation and removal.

In an apparatus that fragments tissue by the ultrasonic vibration of a tool tip, efficiency of energy utilization is optimized when the transducer which provides the ultrasonic vibration operates at resonant frequency. The transducer and surgical tip design establishes the resonant frequency of the system, while the generator tracks the resonant frequency and produces the electrical driving signal to vibrate the transducer at the resonant frequency. However, changes in operational parameters, such as changes in temperature, thermal expansion, and load impedance, result in deviations in the resonant frequency. Accordingly, controlled changes in the frequency of the driving signal are required to track the resonant frequency. This is controlled automatically in the generator.

Conventional ultrasonic surgical aspirating tips employed in surgery for many years typically present a longitudinally vibrating annular surface with a central channel providing suction or aspiration, which contacts tissue and enables fragmentation via described mechanisms of mechanical impact (momentum), cavitation, and ultrasound propagation.

Mechanical impact may be most useful in soft tissue and cavitation clearly contributes to the fragmentation of tenacious and hard tissue in situations where liquids are present and high intensity ultrasound exceeds the cavitation threshold.

Ultrasound propagation is concerned with the transmission of pressure across the boundary of a surgical tip and tissue, which leads to the propagation of pressure and, perhaps more importantly, particle displacement. Acoustic impedance is the total reaction of a medium to acoustic transmission through it, represented by the complex ratio of the pressure to the effective flux, that is, particle velocity times surface area through the medium. As discussed in the classic text of Krautkramer J. and Krautkramer H, *ULTRASONIC TESTING OF MATERIALS*, Berlin, Heidelberg, N.Y., 1983, for the case of a low to high acoustic impedance boundary, it may seem paradoxical that pressure transmitted can exceed 100%, but that is what results from the build-up of pressure from a low to high acoustic impedance boundary. In the case of a high to low acoustic impedance mismatch, such as with a high impedance titanium ultrasonic horn to low impedance fibrous muscle, soft tissue, or water, the pressure transmitted decreases (e.g., less than 15% for titanium to fibrous muscle) and particle displacement increases (e.g., as great as 186% for titanium to muscle).

Conventional ultrasonic surgical aspirating tips have been found to be efficient in the removal of soft tissue, and with emergent bone tips, applicable to the removal of hard tissue; however, some fibrous, elastic, and tenacious tissues persist in difficulty of removal. It has been found that using such conventional ultrasonic horns and devices that employ only the effects of intensification of ultrasound or sharpened edges to remove bovine fibrous muscle tissue, leaves a fibrous elastic skeleton. Thus, there remains a need for ultrasonic surgical devices with innovative aspiration tips that allow for more effective removal of fibrous tissue via the enhanced utilization of ultrasound fragmentation effects.

It is known that materials often fail, fracture, tear, or rupture, more readily as a result of a shear force rather than in tension or compression. Common examples include paper, garden bushes, hair, cloth, steel shear bolts or pins, and collagenous materials. A thin fibrous sheet of paper can be pulled or snapped with a greater tension force, but it can much more easily be ripped by the fingers applying light forces in opposite directions (shear). Likewise, scissors readily cut paper by employing a shear force concentrated by opposing edges of the scissors. Studies of mechanical behavior of materials have shown that biologic tissue is viscoelastic material, meaning that it has a time-dependent stress-strain relationship. The effect of the strain rate on the material is critical to causing fragmentation. The ultrasonic horn of the present invention evolved from imagining innovative ways of introducing scissor or shear ultrasonic effects with a surgical aspirating tip.

Hence, those skilled in the art have recognized a need for an ultrasonic aspiration tip that allows more effective removal of fibrous, elastic, and tenacious tissues. The present invention fulfills this need and others.

SUMMARY OF THE INVENTION

Briefly and in general terms, the present invention is directed to an apparatus and an associated method of fragmenting and removing of target tissue by the introduction of shear stress and the utilization of high strain rates associated with ultrasound. In more detailed aspects, the invention is directed to an ultrasonic surgical aspirating tip that induces a shear stress field, enabling improved fragmentation and aspiration of fibrous, elastic, and tenacious tissues, such as encountered in some tumors or surgical approaches. In yet more detailed aspects, the tip has an innovative pattern about the contacting annulus of adjacent and alternating lands of opposite angles which promote refracted longitudinal waves propagating in greatly different directions at the interface of the contacted fibrous tissue. Refracted longitudinal waves of different directions produce a shear stress field, especially at the intersection of opposite angled lands, and this shear stress enhances fragmentation and removal rate of fibrous tissue.

In accordance with aspects of the invention, there is provided an ultrasonic horn configured for use with an ultrasonic surgical handpiece having a resonator that generates ultrasonic waves, the ultrasonic horn comprising an elongated member having a proximal end, a distal end, and a longitudinal axis, the proximal end being adapted to receive ultrasonic waves from the handpiece, a first land member disposed on an annulus at the distal end of the elongated member, the first land member having a first angle with respect to the longitudinal axis, and a second land member disposed on the annulus, the second land member having a second angle with respect to said longitudinal axis, wherein the first and second angles are different. In more detailed aspects, the first and second land members have opposite first and second angles to each other with respect to the longitudinal axis, the opposite first and second angles are equal and opposite, and the first and second land members are located adjacent each other.

In yet further detailed aspects, the ultrasonic horn further comprises a plurality of land members of different angles alternating around the annulus wherein at least one land member has a blunt edge, whereby cutting is inhibited. The first land member has a first angle of about 10-80°, and the second land member has an opposite second angle of about 10-80° with respect to the longitudinal axis. In another aspect, the first land member has a first angle of about 30-60°, and the second land member has an opposite second angle of about 30-60° with respect to the longitudinal axis. And in yet another aspect, the first land member has a first angle of about 45°, and the second land member has an opposite second angle of about 45° with respect to the longitudinal axis.

In other aspects, the ultrasonic horn is also configured for use with a suction source, wherein the elongated member is hollow and is connected to the suction source, whereby suction is present at the annulus.

In accordance with aspects of an associated method, there is provided a method of applying shear stress to tissue, comprising contacting the tissue at a contact surface, applying energy to the tissue at the contact surface at a first angle with a medical device, and applying energy to the tissue at the contact surface with the tissue at a second angle with the medical device simultaneously with applying energy at the first angle, the second angle being different from the first angle, whereby a shear stress field is created in the tissue. In more detailed aspects, the steps of applying energy comprise applying ultrasonic energy to the tissue at first and second angles with the first and second angles being opposite to each other with respect to a longitudinal axis of the medical device. The steps of applying ultrasonic energy comprise applying ultrasonic energy to the tissue at first and second angles with the first and second angles being equal and opposite to each other with respect to a longitudinal axis of the medical device. Yet further, the steps of applying energy at first and second angles comprise applying ultrasonic energy to the tissue at first and second angles located adjacent each other, whereby a shear stress field is formed in the tissue.

In other method aspects, the steps of applying energy comprise applying ultrasonic energy to the contact surface of the tissue at a plurality of locations at alternating different angles. The steps of applying energy comprise applying ultrasonic energy to the contact surface of the tissue at a first location at an angle of about 45° with respect to a longitudinal axis of the medical device, and applying energy to the contact surface of the tissue at a second location adjacent the first location of the contact surface at about an opposite angle of 45° to the first angle with respect to a longitudinal axis of the medical device. Additionally, the method further comprises applying suction to the tissue at the contact surface to control the position of the tissue during the steps of applying energy to create shear stress.

Other features and advantages of the present invention will become more apparent from the following detailed description of the invention, when taken in conjunction with the accompanying exemplary drawings.

BRIEF DESCRIPTION OF THE DRAWINGS

Embodiments of the presently disclosed shear stress ultrasonic horn are described herein with reference to the drawings, in which.

DETAILED DESCRIPTION OF THE PREFERRED EMBODIMENTS

Embodiments of the presently disclosed ultrasonic horn will now be described in detail with reference to the drawings, in which like reference numerals designate identical or corresponding elements in each of the several views. As used herein, the term "distal" refers to that portion of the instrument, or component thereof which is farther from the user while the term "proximal" refers to that portion of the instrument or component thereof which is closer to the user during normal use. The terms "ultrasonic horn," "ultrasonic aspirating tip," "aspirating tip," "ultrasonic surgical tip," and "surgical tip" are used herein interchangeably.

Figure 1:
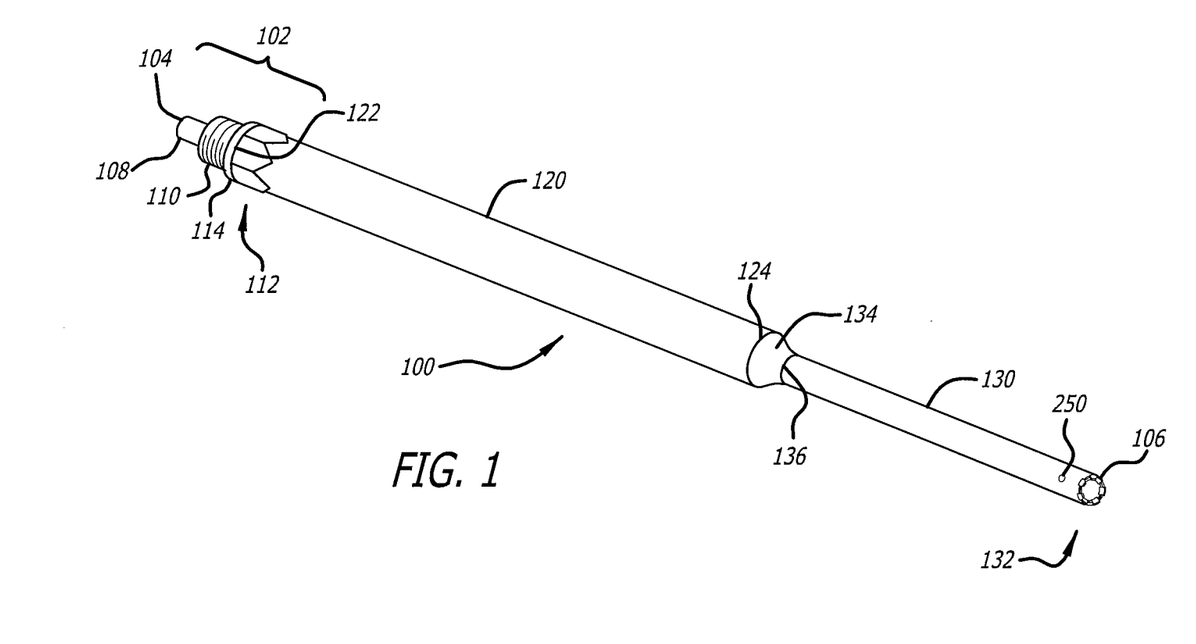
FIG. 1 is a perspective view of an ultrasonic horn in accordance with aspects of the present invention in which the horn includes an extension member, an elongated member, and a tip distal end having a particular configuration for establishing shear stress in target material, and further includes an adapter at its proximal end for connection with an ultrasonic energy source.

Referring now to FIG. 1 in more detail, there is shown an ultrasonic horn 100, in accordance with one embodiment of the present disclosure. The ultrasonic horn is adapted for use in an ultrasonic surgical system having an ultrasonic handpiece. An example of such an ultrasonic surgical system is disclosed in U.S. Pat. No. 6,214,017 to Stoddard et al., the entire contents of which are incorporated herein by reference. Alternatively, the ultrasonic horn 100 may be adapted for use with the ultrasonic surgical system disclosed in U.S. Pat. No. 4,063,557 to Wuchinich et al., the entire contents of which are incorporated herein by reference.

The ultrasonic horn 100 of FIG. 1 includes a proximal end 104 and a distal end 106. At the proximal end the horn comprises an adapter 102 that includes, extending from the proximal end 104 towards the distal end 106, a shaft 108, a threaded member 110, and a flange 112 terminating at the distal end 106. The flange 112 includes a leading edge 114.

Figure 2:
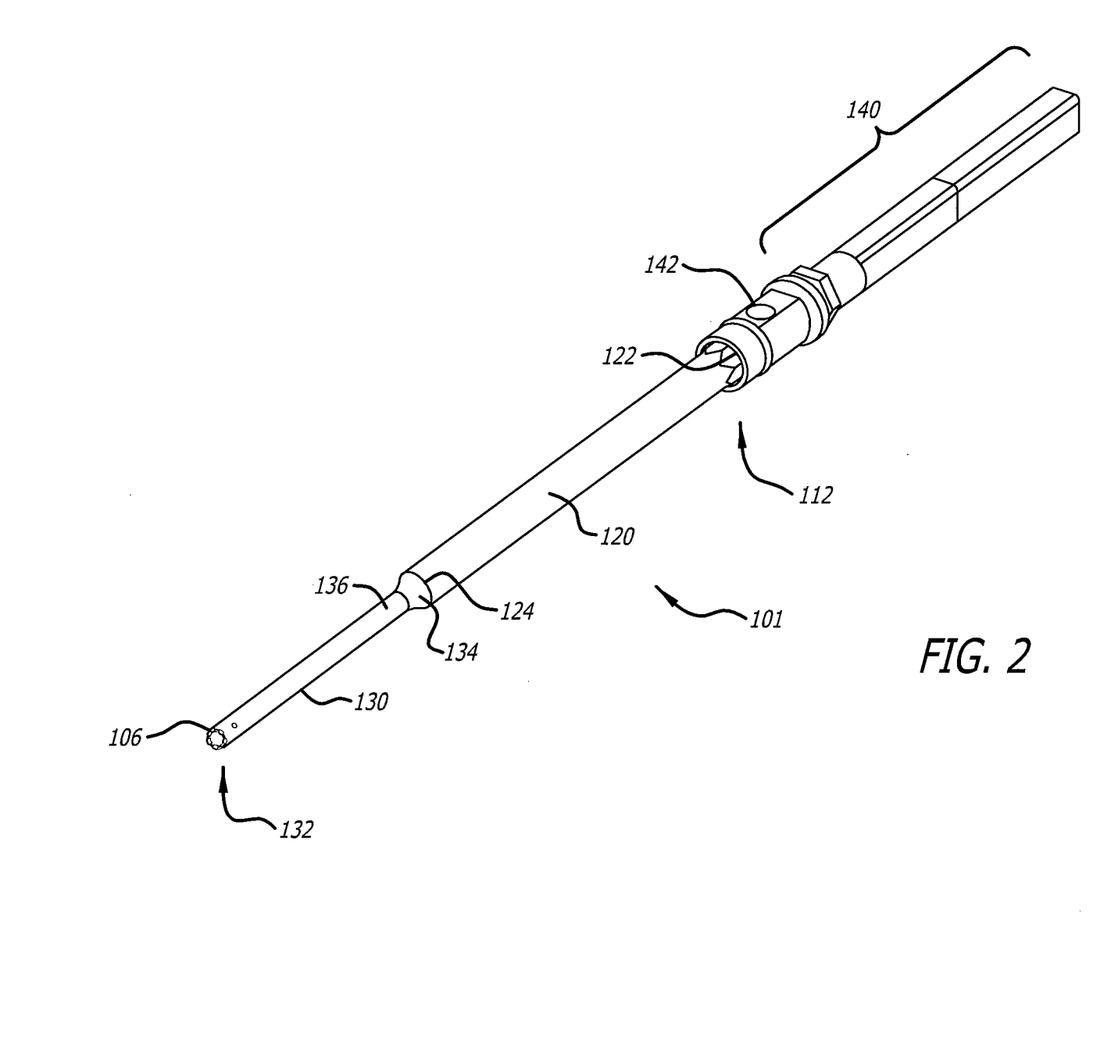
FIG. 2 presents a perspective view of an ultrasonic horn similar to FIG. 1 but having a curve in its extension member to enable better viewing of target tissue during use, the horn also showing actual connection to an ultrasonic energy generator at its proximal end.

The proximal end 104 of the adapter 102 is configured to connect the ultrasonic horn 100 to an ultrasonic handpiece or resonator. Referring also now to FIG. 2, the connection of an ultrasonic horn to a resonator 140 is shown. FIG. 2 shows a horn 101 similar to the horn 100 of FIG. 1 with the exception that the horn 101 of FIG. 2 is curved at an angle of approximately 13°. The base designs of such horns include both curved and straight surgical tips, i.e. the profiles may be the same. The surgical curved tips are bent on a mandrel following machining. The bend can be about 13° or less. Curved surgical tips are often preferred because the handpiece is moved out of the field of view of the microscope used by the surgeon viewing the distal end. The curve in the embodiment of FIG. 2 is formed in an extension member 120 of the horn, as described below in further detail.

The resonator 140 is connected to the adapter 102 of the horn through a connecting body 142 in this embodiment. As used herein, the term "resonator" refers to what is often referred to in the literature as an ultrasonic handpiece. The resonator is typically a laminated core-stack of Permanickel. Those skilled in the art will recognize that the threaded member 110 is identified herein in one embodiment as an externally threaded member for connection to internal threads of the connecting body 142 and/or to an ultrasonic resonator 140 but that other connection types can be implemented to connect to the connecting body and/or ultrasonic resonator. Such connection types include but are not limited to welds, socket couplings, and compression couplings. Because such resonators and connections are well known to those skilled in the art, no further details are provided here.

The ultrasonic horns 100 and 101 both include an extension member 120 having a proximal end 122 that coincides with the flange 112 of the adapter 102. The extension member 120 also has a distal end 124. The horn further comprises an elongated member 130 with a distal tip 132 at the distal end 106 of the horn. The distal end 124 of the extension member terminates in a transition segment 134 to the elongated member 130. The proximal end 136 of the elongated member is located at the distal side of the transition segment 134 while the distal end of the extension member is located at the proximal side of the transition segment. The distal end of the elongated member 130 is configured as the distal tip 132.

The connecting body 142 is configured to connect the resonator 140 to the horn 101 so that ultrasonic energy may be applied to the horn and conducted to a target site. In one embodiment, the resonator 140 includes a magnetostrictive transducer, although other transducer types can be included such as a piezoelectric transducer. The resonator 140 is supplied power from a power generator (not shown) such that the resonator 140 operates at a target frequency, e.g., in the range of about 23,000 Hz (23 kHz), 36 kHz, or other. Utilizing a piezoelectric transducer will provide similar ultrasonic properties and alternate frequencies for higher stroke and power (e.g., 23 kHz and 24 kHz devices). It is important to note that use of alternative transducers or ultrasonic frequencies will not substantially deviate from the innovative principles of the shear stress ultrasonic horn disclosed herein. In one embodiment, the ultrasonic horns 100 and 101 are made of titanium, although other materials such as stainless steel may be used. In a preferred embodiment, the titanium ultrasonic horn is nitride coated to improve hardness and improve wear resistance.

Figure 3:
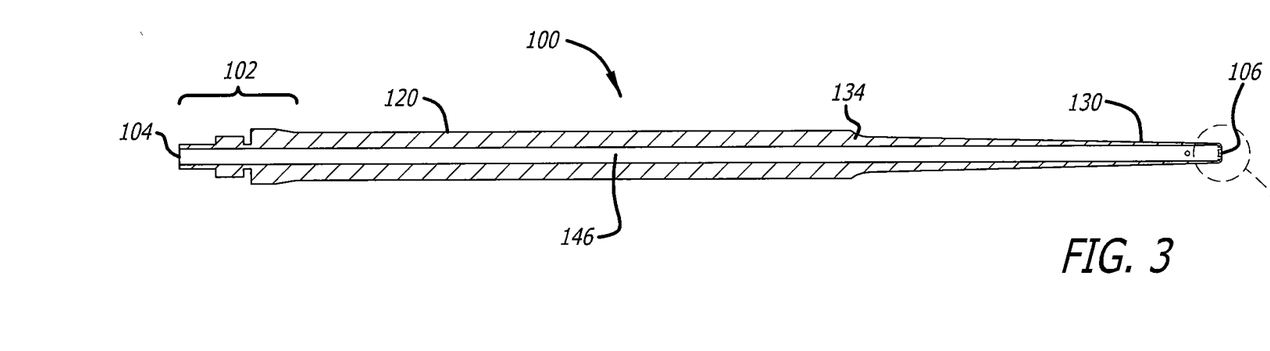
FIG. 3 shows a cross-sectional view of the horn of FIG. 1 showing the aspiration channel formed completely through the horn, in this embodiment.

As best seen in FIG. 3, which is a longitudinal cross-sectional view of the ultrasonic horn 100 of FIG. 1, an internal channel 146 is formed longitudinally through the entire horn, i.e., from the distal end 106 to the proximal end 104. As is known in the art, the channel terminates in the connecting body 102, and does not continue into the resonator (not shown). In some embodiments, the channel may be coupled to a side port or other device to introduce fluid into the channel or withdraw fluid from the channel by means of suction or vacuum. In some implementations, the central channel supports aspiration or suction of tissue. The internal channel can provide suction when connected with a vacuum source at the console. The suction can be used to control the position of target tissue. For example, suction may be used to draw target tissue to the distal tip of the horn for coupling and contact to the tissue for efficient fragmentation. The internal channel shown and described herein also aids in cooling, where irrigation liquid is caused to flow through the channel.

The internal channel 146 also affords greater mechanical gain for the horn 100 and 101 because the gain is dependent on the reduction in area ratio of the thin walls. A purpose of the internal channel 146 is to support gain for surgical tips with the contacting annulus distal ends 160.

Figure 4:
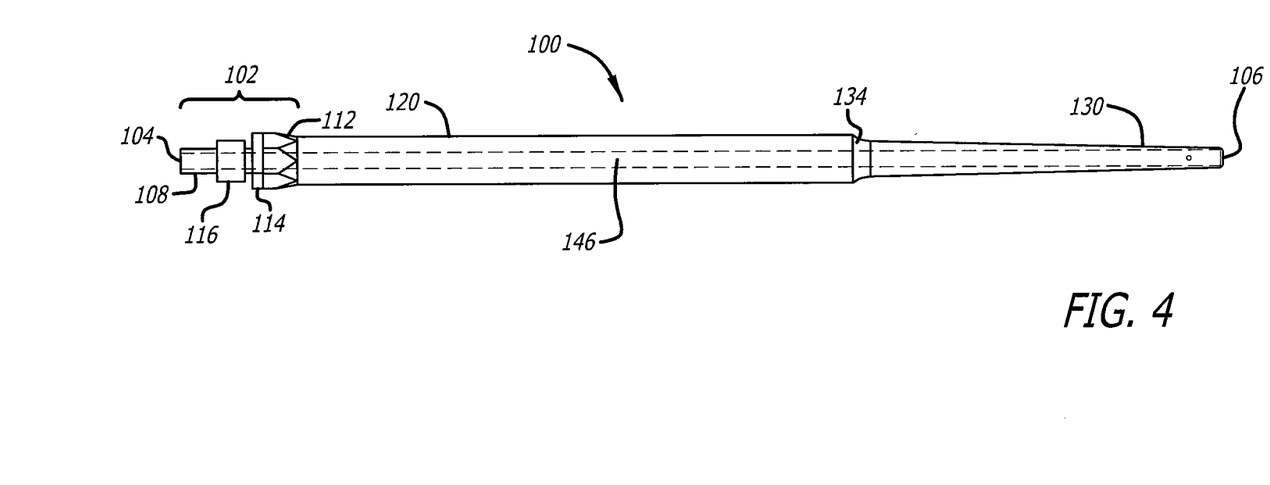
FIG. 4 is a partial cross-sectional view of the horn of FIG. 1 showing further detail of the adapter configuration at the proximal end of the horn.

Referring now to FIG. 4, a top view of the ultrasonic horn 100 of FIG. 3 is shown with the channel 146 shown in phantom lines. The adapter 102 is also shown in partial cross-section. As is clearly shown, the internal channel 146 is also formed within the adapter 102 and throughout the remainder of the horn 100.

Figure 5:
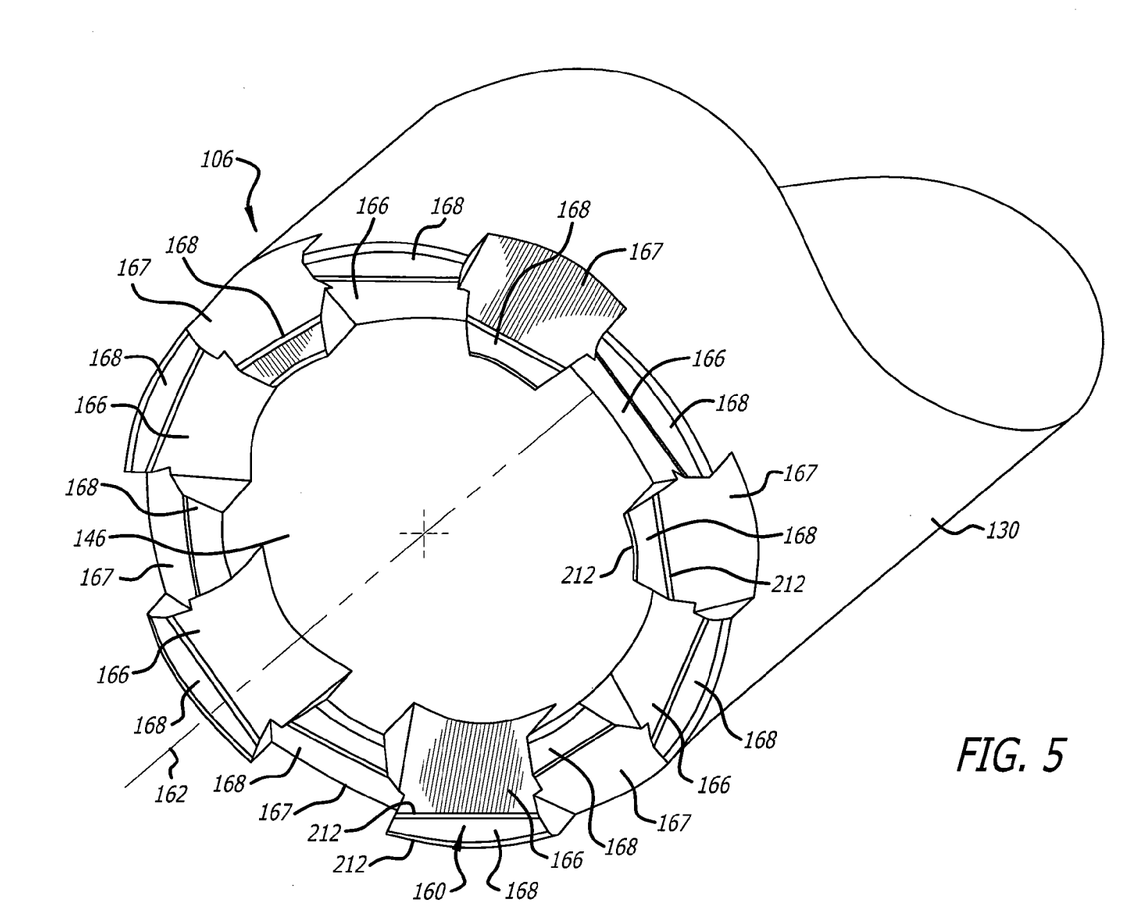
FIG. 5 is a perspective, more detailed view of the distal tip annulus at the distal end of the horns of FIGS. 1 and 2 showing a configuration of features used to create shear stress in target tissue, in this case, a plurality of lands set at alternating angles to adjacent lands.

As a preferred embodiment illustrated in FIG. 5, the distal end 106 of the ultrasonic horn 100 is shown, and in particular, a contacting annulus 160 disposed at the distal tip of the elongated member 130 is shown in detail. The contacting annulus 160 is formed of a plurality of faces 168 formed at the distal ends of the lands 166 and 167 having differing angles in relation to a longitudinal centerline 162. In this embodiment, the contacting annulus 160 has twelve lands 166 and 167, each with a face 168 at the annulus. Although only two lands 166 and 167 are indicated with shading, and only one face 168 is indicated with shading, this is for clarity of illustration purposes only. Each land and each face is meant to be indicated; only a few representative ones were picked for shading.

The contacting annulus 160 In FIG. 5 has a number of lands 166 having an angle directed toward the longitudinal axis 162 uniformly interspaced with an equal number of lands 167 having an angle directed away from the longitudinal axis 162. In this embodiment, there are six lands 166 angled towards the center longitudinal axis that are uniformly interspersed with six more lands 167 angled away from the center longitudinal axis. Therefore, each land is located between two lands having the opposite angle (directed toward the axis or away from the axis, as the case may be). In this embodiment, the lands are in contact with adjacent lands and have opposite angles from each other. As an example, in the set of lands angled toward the longitudinal axis, each land has an angle of +45°. The alternating and uniformly interspersed adjacent lands have an angle with regard to that same longitudinal axis of −45°, thereby having an opposite angle. Other angles of alternating lands may be used, fewer or more lands may be used at the contact annulus, the spacing between lands may vary, and different configurations are possible.

It has been found that adjacent lands of opposite angles promote refracted longitudinal waves propagating in different directions at the interface to the tissue to establish shear forces. Refracted longitudinal waves of different directions produce a shear stress field, especially at the intersection of opposite angled lands 166 and 167, and this shear stress enhances fragmentation and the removal rate of fibrous tissue. Ultrasound can be further intensified (power per unit area increased) due to the tapering of the adjacent lands, although distal ends or faces 168 are left blunt in one embodiment, so that wear is minimized and tissue is fragmented with ultrasound energy rather than cut, which could cause clogging of the central aspiration channel 146.

Figure 6:
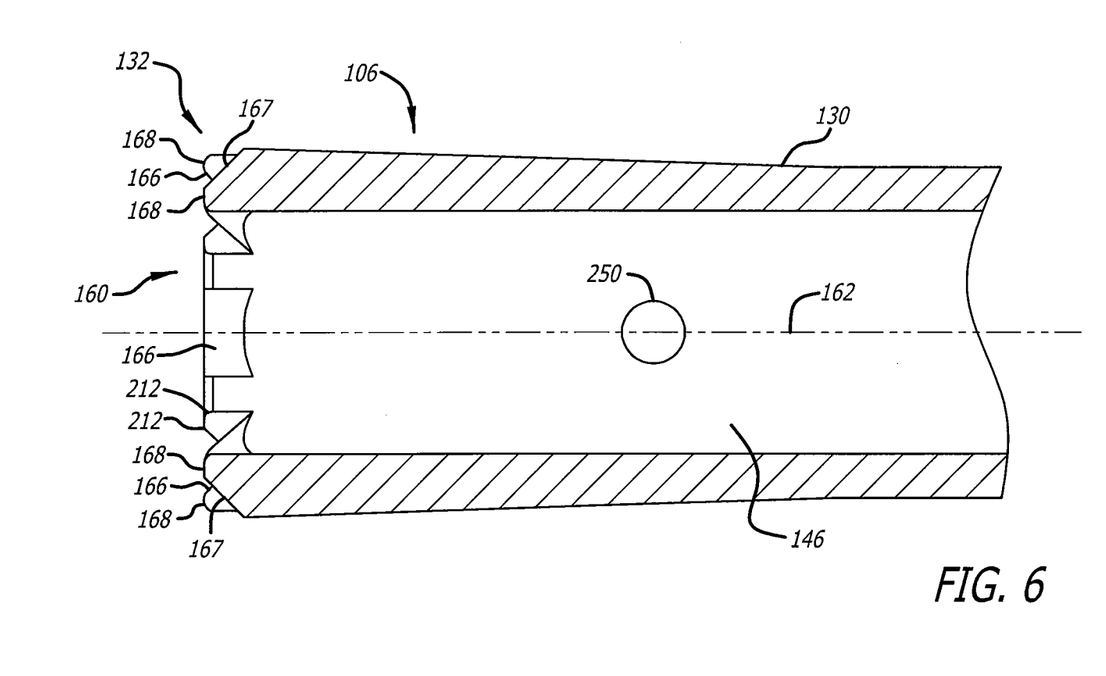
FIG. 6 is a side view of the distal tip annulus of FIG. 5 showing the relationship of alternate angled lands.

FIG. 6 presents a side view of the annulus 132, distal tip 106, and lands 166 and 167 of FIG. 5. In particular, portions of two outwardly-extending lands 167 are shown in cross section, one at the top of the figure and one at the bottom. Behind each of these and rotated around the annulus 160 by approximately 30° is a land 166 of opposite angle extending inwardly. The remaining three lands of alternating opposite angles are shown located around the annulus. Also shown is a pre-aspiration aperture 250 through which fluid may be drawn through the internal channel 146 of the horn.

FIGS. 5 and 6 also show the feature of rounding or blunting 212 the lands 166 and 167 so that sharpness is removed. In this case, the dimension of the blunting is 0.005 inches (0.127 mm). The drawing numeral 212 is only shown in a few places on FIGS. 5 and 6 so as to not lessen clarity of the figure; however, it is meant to apply to the other lands as well.

It is known that the angle of refraction of the longitudinal wave can be ideally calculated based on Snell's Law, and it is dependent on the incident angle and difference in acoustic velocity of titanium (the material of the horn in one embodiment) and the medium or media encountered at the boundary, e.g., soft tissue, fibrous muscle, water, etc. An illustration of the ultrasonic horn to tissue interface for adjacent lands of opposite angles is provided in FIGS. 7-10 for an assumed dominantly directed extensional wave along the longitudinal axis of the surgical tip. For a +45° and −45° interface of the titanium lands 166 and 167 of opposite angles to tissue 180, the refracted longitudinal wave angles were calculated for air, water, soft tissue, muscle, and bone employing representative material properties from the literature. Most pertinent, a 13° refracted longitudinal wave angle is calculated for titanium to muscle.

Figure 7:
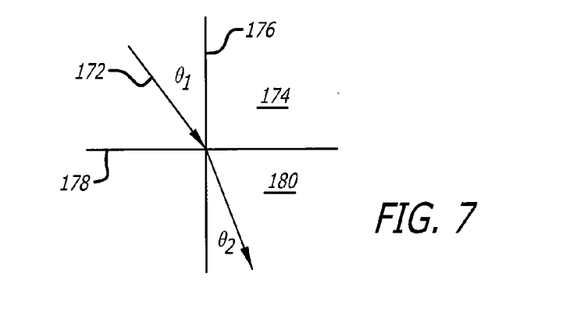
FIG. 7 is a basic diagram showing the operation of Snell's law at the interface of two different materials, one of which is the material of the ultrasonic horn and the other of which is the material of target tissue.

In FIG. 7, the basic principle of refraction is illustrated. The ultrasonic energy 172 is propagating in titanium 174 at an angle of $\theta_1$ to the ordinate axis 176. Upon reaching the boundary 178 (abscissa axis) with fibrous tissue 180, the ultrasonic energy 172 is refracted by 13°. Therefore $\theta_2 = \pm 13°$ as measured from the normal to the interface.

Figure 8:
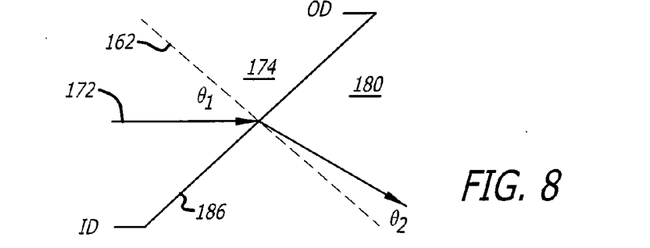
FIG. 8 is a schematic diagram showing the refraction of ultrasonic energy from a land formed at the annulus at the tip of the distal end of an ultrasonic horn, the land being oriented at a first angle of +45°.

FIG. 8 presents a diagram of a titanium land 186 having an inner diameter ID and an outer diameter OD. Ultrasonic energy 172 is propagating through the land at an angle of $\theta_1 = +45°$ to the centerline 162 through the land. Upon reaching the boundary 186 with fibrous tissue 180, refraction occurs and the ultrasonic energy then has an angle of $\theta_2$ with the centerline 162, where $\theta_1 \neq \theta_2$.

Figure 9:
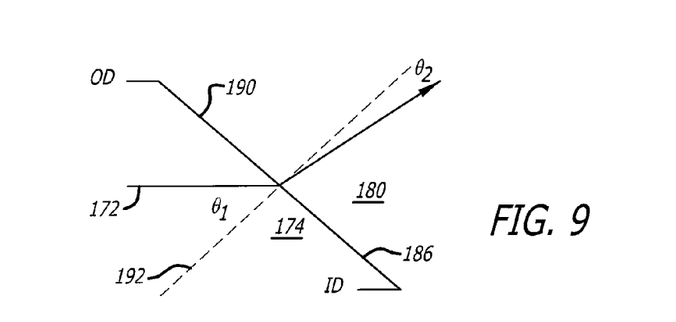
FIG. 9 is a schematic diagram showing the refraction of ultrasonic energy from a land formed at the annulus at the tip of the distal end of an ultrasonic horn, the land being oriented at a second angle of −45° (which is opposite the first angle)

FIG. 9 presents a diagram of a titanium land 190 having the opposite land angle than that of the land 186 in FIG. 7. The land 190 has an inner diameter ID and an outer diameter OD. Ultrasonic energy 172 is propagating through the land at an angle of $\theta_1 = -45°$ to the centerline 192 through the land. Upon reaching the boundary 186 with fibrous tissue 180, refraction occurs and the ultrasonic energy then has an angle of $\theta_2$ with the centerline 192, where $\theta_1 \neq \theta_2$.

Figure 10:
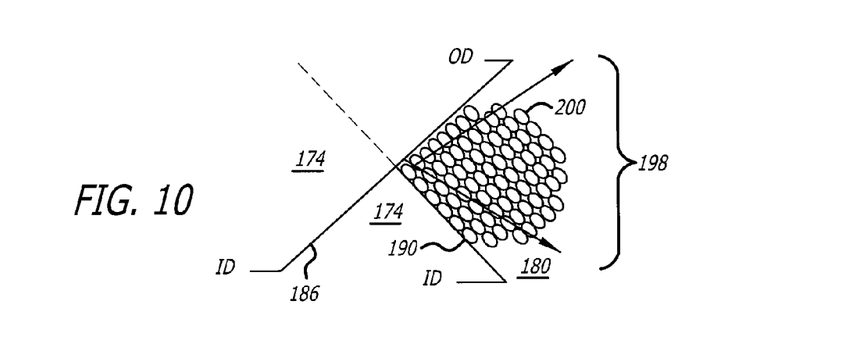
FIG. 10 is an illustration of the propagation of a shear stress field through adjacent cells located about the apex of the land members of FIGS. 8 and 9 that results when the refracted waves of the first land member (FIG. 8) are coupled with the refracted waves of the second and adjacent land member (FIG. 9)

FIG. 10 is a drawing showing the land 186 of FIG. 8 in front of the land 190 of FIG. 9 with the refracted ultrasonic energy of each creating a shear stress field 198. Due to the adjacent lands 186 and 190 being of opposite angles, there will be component waves causing shear 198. Refracted longitudinal waves of different directions produce a shear stress field, especially at the intersection of opposite angled lands, and this shear stress enhances fragmentation and removal rate of fibrous tissue 180. Adjacent cells or particles 200 about the intersection of the lands could experience displacement or particle motion with 64° of shear. It is important to note that due to the adjacent lands being of opposite angles (in this case +45° and −45°), there will always be component waves propagating at opposite angles that will subject the fibrous tissue to shear stress.

In a preferred embodiment, the shear stress tip implementation of adjacent opposite angled lands 186 and 190 does not compress tissue 180. Ultrasound energy 172 from adjacent opposite angled lands does not cancel due to destructive interference. However, opposing faces would cancel ultrasound energy due to destructive interference and would cause compression of tissue.

It has been found that although a shear wave component may exist and aid in fragmentation when coupled via solids, refracted longitudinal waves exist and will couple even in liquid, such as water or saline solution supplied as irrigation liquid via the surgical tip flue or channel 146. Shear waves will not propagate directly in gases and liquids. Shear stress is not wholly or largely dependent on coupling of a shear wave, but rather would be promoted by refracted longitudinal waves of opposite angles.

Increasing the angle to 60° from 45° between the lands 166, 167 and the tissue would typically increase shear angle but reduce transmitted particle displacement. Reducing the land angle between the lands 166, 167 and the tissue from 45° to 30° would reduce shear angle but increase particle displacement. Given that particle displacement calculated exceeds 130% for angles from 30° to 60°, the selection of angle may be dominated by shear angle and ease of manufacturing. Alternative angles could be selected without substantially deviating from the shear stress tip principle of operation.

Proof of principle was demonstrated with production viable shear stress ultrasonic horns yielding as great as 50% improvement in removal rate of bovine fibrous muscle compared to standard surgical tips and devices with distal-ends that employed only intensification of ultrasound or sharpened edges. Conventional ultrasonic surgical aspirating tips are efficient in removal of soft tissue, and with emergent bone tips, applicable to hard tissue; however, some fibrous, elastic, and tenacious tissues persist in difficulty in removal. A particular advantage of the shear stress ultrasonic horn is that it provides improvement in the removal rate of fibrous tissue via enhanced utilization of ultrasound fragmentation effects.

Figure 11:
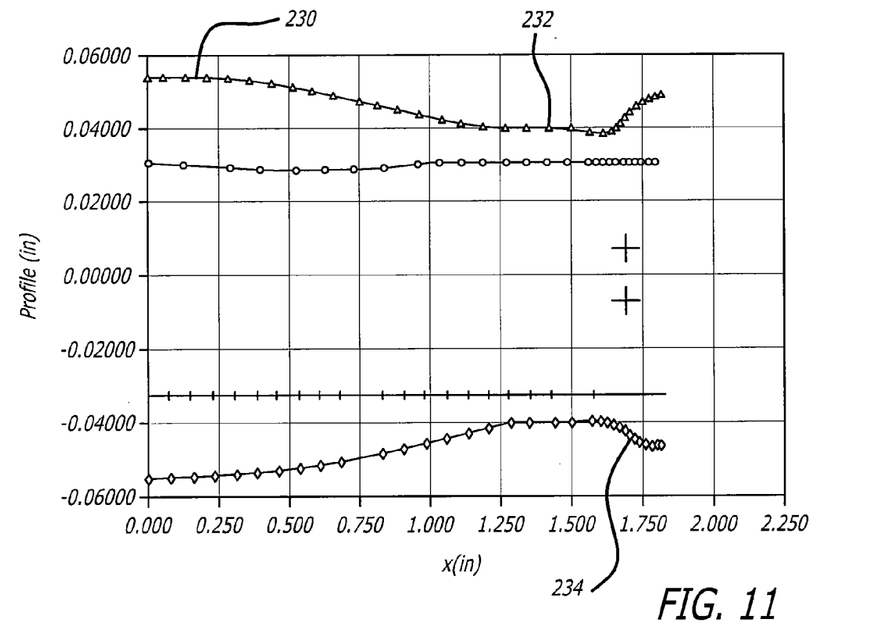
FIG. 11 is a graph of the ultrasonic horn radius versus horn length for a target frequency of 36 kHz, shown in area function of the Gaussian shape.

FIG. 11 illustrates a shear stress tip profile 230. Area function of the Gaussian is shown, and it influences the resonant frequency and the mechanical gain. A blend is provided to a short straight section 232. A flared exponential profile 234 of the horn expands the wall thickness suitably for machining of the distal end of the shear stress tip comprising a plurality of lands as shown in FIGS. 5 and 6, as one embodiment.

Figure 12:
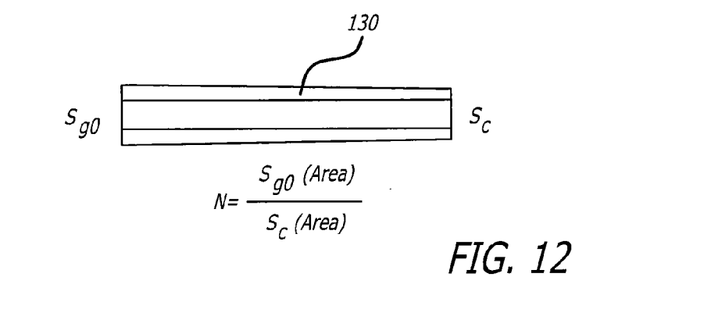
FIG. 12 presents a diagram of the shape of an ultrasonic horn.

In FIG. 12, the elongated member 130 is tapered such that the cross-sectional area $S_{go}$ is a maximum at the proximal end 136 interfacing with the transition segment 134 and is a minimum $S_c$ at the tip 132. An area function is defined as N where $N = S_{go}/S_c$ and is the area ratio of the Gaussian portion, and it establishes gain. The ultrasonic wave is supported by particle motion in the titanium. The particles are vibrating about their neutral position in a longitudinal or extensional wave. The particles do not move along the length of the horn, but only vibrate, just as a cork or bobber shows that a wave passes through water via the liquid. As the horn wall thickness decreases, more strain occurs in the metal as the particles move a greater distance about their neutral position. The displacement of the end of the horn is due to strain along the horn. All the particles supporting the wave are moving at the same resonant frequency. The greater the strain, the greater the velocity of the particles necessary to maintain the same frequency.

Mechanical gain in the ultrasonic horn 100 is maximized within acceptable stress limits of the titanium with stepped horn, Gaussian horn, blended short straight section, and flared exponential profiles. CUSA® (Integra LifeSciences Corporation, Plainsboro, N.J.) Ampulla (Gaussian) profile affords multiplying the gain of the stepped horn with a uniform distribution of stress, and this profile coupled with a blend to short straight section and flared exponential provide high-gain and forward propagation of ultrasound with minimal errant reflection or standing waves that could limit transmitted ultrasound, increase power requirements, or reduce horn stroke amplitude. These horn profiles promote high mechanical gain, forward propagation of ultrasound, and commensurate surgical tip distal-end stroke.

Stroke amplitude was not sacrificed in adapting to a larger wall thickness distal end for 36 kHz shear stress tip; in fact, prototype horn stroke exceeded the commercial baseline. This was accomplished with optimization of the Gaussian profile and blend to the straight section. Stroke peak-to-peak of the prototypes was 196 μm (0.0077 in) versus 183 μm (0.0072 in).

Figure 13:
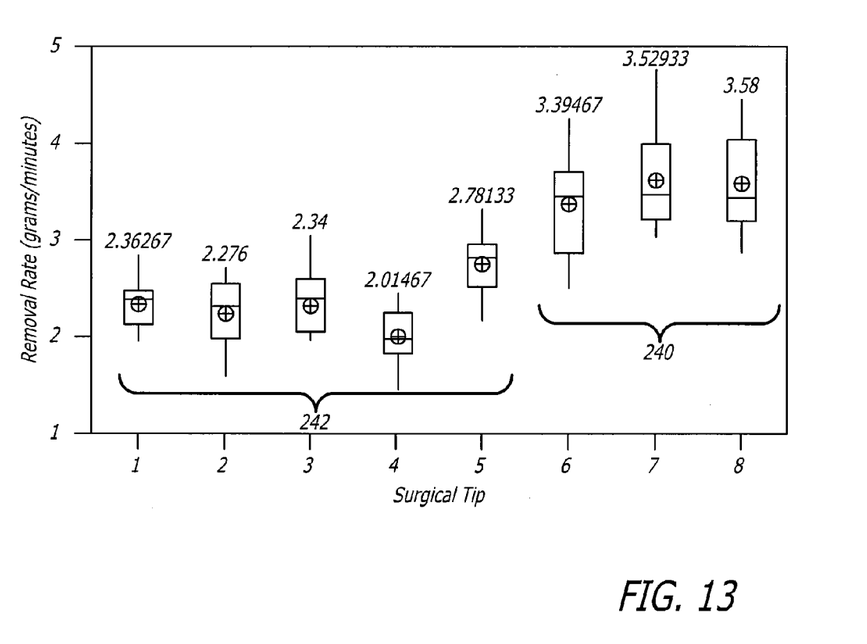
FIG. 13 provides a chart of comparative test data obtained from use of the ultrasonic horn of FIG. 1 compared to the use of ultrasonic horns of more conventional geometries, showing an improvement in results with the horn of FIG. 1.

Proof of principle of the ultrasonic horn 100 with the contact annulus exemplified in FIG. 5 was demonstrated with production viable prototypes of about 35.75 kHz yielding as great as a 50% improvement in removal rate of bovine fibrous muscle compared to standard ultrasonic horns and devices that employed only intensification of ultrasound or sharpened edges. Preliminary comparative data are exhibited in FIG. 13, based on fifteen measurements per surgical tip type. Baseline surgical tips included representative commercial CUSA EXcel® 36 kHz Extended MicroTip™, High-Stroke Extended MicroTip™ (Integra LifeSciences Corporation, Plainsboro, N.J.) and devices with more simply angled, grooved, or beveled ends. The ultrasonic shear stress horns of the present invention are referred to as numeral 240 in the chart. Along with preliminary quantitative data, qualitative observations of removal of bovine muscle indicate elimination of fibrous elastic structure where conventional aspirating tips 242 left a fibrous elastic skeleton. The mean values are printed next to the icons in the chart. The mean values indicated as great as a 50% increase in removal rate for the shear stress horns 240.

In one embodiment, pre-aspiration apertures or holes 250 (FIGS. 1 and 6) are formed through opposing sides of the elongated member 130 wall on opposing sides of a straight or constant diameter portion. Pre-aspiration apertures may be employed in conjunction with the internal channel 146, which, as previously noted, extends from the proximal end 104 to the distal tip 132. The pre-aspiration holes 250 can be optionally used to suction a portion of the irrigation liquid employed through the channel to aid in cooling the tip. The pre-aspiration holes can also reduce misting caused by cavitation at the distal end of tip, thereby improving viewing via endoscopes or microscopes.

In terms of applications, the ultrasonic horn 100 is useful for cranial-based surgery, and when performing transsphenoidal or endoscopic-nasal approaches. The ultrasonic horns 100 and 101 of the present disclosure can be combined with irrigation and aspiration systems such as is disclosed in, for example, FIG. 3 of U.S. Pat. No. 6,214,017 B1 to Stoddard et al., which as noted is incorporated by reference herein in its entirety. Irrigation in the internal channel 146 aids in cooling the material of the horn which is in flexure. Pre-aspiration holes may also aid in cooling. The cooling capability can be enhanced by suctioning some portion of the irrigation liquid through the internal channel 146 of the horn 100 or 101 via pre-aspiration.

As used herein, "vacuum" is meant to include partial vacuum or lowered pressure. The term "angled inwardly" is meant to indicate that the angle is formed on the inside surface of the contact annulus. The term "angled outwardly" is meant to indicate that the angle is formed on the outside surface of the contact annulus. Additionally, the term "lands" is meant to refer to the surface commonly given this name in the art and is also meant to refer to other surfaces that perform the same function.

The invention may be embodied in other forms without departure from the scope and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention.

We claim:

1. A method of producing a shear stress field for application to a contact surface of biological tissue, the method comprising:

simultaneously applying energy to a plurality of lands that are located on an annulus of a distal tip of a medical device, the distal tip having a longitudinal axis, the lands alternating between having an inclined configuration facing toward the longitudinal axis in reference to the distal tip and having a declined configuration facing away from the longitudinal axis in reference to the distal tip wherein each land having the inclined configuration has on either side of it a land having the declined configuration and each land having the declined configuration has on either side of it a land having the inclined configuration;

wherein energy from each land to which energy was simultaneously applied crosses energy from its adjacent lands;

wherein the crossing energy from adjacent lands of different configurations forms a shear stress field between the two energies that may be applied to the contact surface of biological tissue.

2. The method of producing a shear stress field of claim 1, wherein the step of simultaneously applying energy comprises simultaneously applying energy to the lands wherein all lands having an inclined configuration and all lands having a declined configuration have first and second angles respectively with the first and second angles being opposite to each other.

3. The method of producing a shear stress field of claim 2, wherein the step of simultaneously applying energy comprises simultaneously applying energy to the lands wherein all lands having the inclined configuration and all lands having the declined configuration have first and second angles respectively with the first and second angles being equal and opposite to each other.

4. The method of producing a shear stress field of claim 1, wherein the step of simultaneously applying energy comprises simultaneously applying energy to the plurality of lands, wherein each land has a blunt distal end.

5. The method of producing a shear stress field of claim 1, wherein the step of simultaneously applying energy comprises simultaneously applying energy to the plurality of lands, wherein each land having the inclined configuration has an angle of about 45° with respect to a reference point, and each land having the declined configuration has an opposite angle of about 45° to the inclined lands with respect to the reference point.

6. The method of producing a shear stress field of claim 1, further comprising applying suction at the distal tip of the medical device during the step of applying energy to create the shear stress field.

7. The method of producing a shear stress field of claim 1, wherein the step of simultaneously applying energy comprises simultaneously applying energy to the lands wherein the lands are configured such that they adjoin each other.

8. The method of producing a shear stress field of claim 1, wherein the step of simultaneously applying energy comprises simultaneously applying energy to the plurality of lands that have been located at the annulus at the distal tip of the medical device wherein the medical device is elongated.

9. The method of producing a shear stress field of claim 1, wherein the step of simultaneously applying energy to the lands comprises simultaneously applying energy to lands located on the distal tip of the medical device, wherein the annulus is completely formed of lands.

10. The method of producing a shear stress field of claim 1, wherein the step of simultaneously applying energy to the lands comprises simultaneously applying energy to adjacent lands wherein a first land has the inclined configuration and an adjacent land has the declined configuration, wherein the adjacent lands point in opposite directions without pointing at each other.

11. A method of producing a shear stress field for application to a contact surface of biological tissue, the method comprising:

simultaneously applying energy to a plurality of lands that completely form an annulus of a distal tip of an elongated medical device, the distal tip having a longitudinal axis, all lands alternating between having an inclined configuration facing toward the longitudinal axis in reference to the distal tip and having a declined configuration facing away from the longitudinal axis in reference to the distal tip wherein each land having the inclined configuration has on either side of it a land having the declined configuration and each land having the declined configuration has on either side of it a land having the inclined configuration wherein energy from each adjacent land to which energy was simultaneously applied crosses each other forming a shear stress field between the two energies of adjacent lands that may be applied to the contact surface of biological tissue to create shearing stresses therein.

12. The method of producing a shear stress field of claim 11, wherein the step of simultaneously applying energy to the lands comprises simultaneously applying energy to all lands which completely fill the annulus tip such that the lands adjoin each other.

13. The method of producing a shear stress field of claim 11, wherein the step of simultaneously applying energy to the lands comprises simultaneously applying energy to adjacent lands wherein a first land has the inclined configuration and an adjacent land has the declined configuration, wherein the adjacent lands point in opposite directions without pointing at each other.

14. The method of producing a shear stress field of claim 11, wherein the step of simultaneously applying energy comprises simultaneously applying energy to the plurality of lands, wherein each land having the inclined configuration has an angle of 45° toward a reference point, and each land having the declined configuration has an angle of 45° directed away from the reference point.

15. The method of producing a shear stress field of claim 11, further comprising the step of applying suction at the distal tip of the medical device during the step of applying energy to create the shear stress field.

16. The method of producing a shear stress field of claim 11, wherein the step of simultaneously of applying energy comprises simultaneously applying energy to the plurality of lands, wherein each land has a blunt distal end.

* * * * *